(12) United States Patent
Nishino et al.

(10) Patent No.: US 8,093,378 B2
(45) Date of Patent: Jan. 10, 2012

(54) CRYSTALLIZATION METHOD FOR INTERMEDIATES OF CARBAPENEM ANTIBIOTICS

(75) Inventors: Keita Nishino, Takasago (JP);
Teruyoshi Koga, Takasago (JP);
Masafumi Fukae, Osaka (JP);
Yasuyoshi Ueda, Osaka (JP)

(73) Assignee: Kaneka Corporation, Osaka (JP)

( * ) Notice: Subject to any disclaimer, the term of this patent is extended or adjusted under 35 U.S.C. 154(b) by 408 days.

(21) Appl. No.: 12/226,771

(22) PCT Filed: Apr. 18, 2007

(86) PCT No.: PCT/JP2007/058404
§ 371 (c)(1),
(2), (4) Date: Oct. 28, 2008

(87) PCT Pub. No.: WO2007/125788
PCT Pub. Date: Nov. 8, 2007

(65) Prior Publication Data
US 2009/0118496 A1    May 7, 2009

(30) Foreign Application Priority Data

Apr. 28, 2006 (JP) .................................. 2006-125478

(51) Int. Cl.
*C07F 9/568* (2006.01)
(52) U.S. Cl. ........................................ 540/350
(58) Field of Classification Search ............ 540/350
See application file for complete search history.

(56) References Cited

U.S. PATENT DOCUMENTS

| | | | |
|---|---|---|---|
| 4,707,547 A * | 11/1987 | Christensen et al. | 540/310 |
| 4,888,344 A | 12/1989 | Sunagawa et al. | |
| 4,925,836 A * | 5/1990 | Kumagai et al. | 514/210.11 |
| 4,992,542 A * | 2/1991 | Christensen et al. | 540/350 |
| 5,550,121 A * | 8/1996 | Nakagawa et al. | 514/210.12 |
| 5,602,118 A * | 2/1997 | Lin et al. | 514/210.11 |
| 2003/0153191 A1* | 8/2003 | Saitoh et al. | 438/694 |
| 2004/0198973 A1* | 10/2004 | Masahiko et al. | 540/350 |
| 2004/0235817 A1* | 11/2004 | Brands et al. | 514/210.13 |

FOREIGN PATENT DOCUMENTS

| | | |
|---|---|---|
| EP | 0 289 801 | 11/1988 |
| JP | 64-79180 | 3/1989 |
| JP | 1-268688 | 10/1989 |
| JP | 4-330085 | 11/1992 |
| JP | 6-321946 | 11/1994 |
| JP | 8-311092 | 11/1996 |
| JP | 10-195076 | 7/1998 |
| JP | 2000-44587 | 2/2000 |
| JP | 3080417 | 6/2000 |
| JP | 2003-26680 | 1/2003 |
| JP | 3479720 | 10/2003 |
| JP | 2005-508321 | 3/2005 |
| WO | 03/026572 | 4/2003 |

OTHER PUBLICATIONS

Nagao, Journal of Organic Chemistry (1992), 57(15), 4243-9.*
Shih, Heterocycles (1984), 21(1), 29-40.*
Machine translation of JP 06-321946 (1994).*
Machine translation of JP 2000-044587 (2000).*
Machine translation of JP 08-311092 (1996).*
Translation of JP 04-330085 (1992).*
International Search Report dated Jul. 17, 2007 in the International (PCT) Application PCT/JP2007/058404 of which the present application is the U.S. National Stage.
Forms PCT/IB/338 and 373 together with English translation of PCT Written Opinion dated Nov. 27, 2008 in International (PCT) Application No. PCT/JP2007/058404.
Supplementary European Search Report issued May 3, 2011 in corresponding European Application No. 07 74 1840.

* cited by examiner

*Primary Examiner* — Mark Berch
(74) *Attorney, Agent, or Firm* — Wenderoth, Lind & Ponack, L.L.P.

(57) ABSTRACT

An improved crystallization method for an azetidinone compound represented by the formula 1:

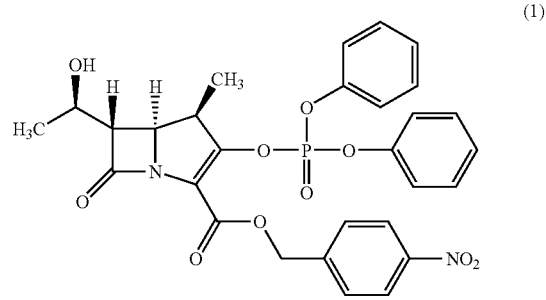

(1)

, which is extremely useful as a common intermediate for the synthesis of 1β-methylcarbapenem compounds. The present method provides crystals having higher quality and stability than conventional crystals and excellent filterability at the time of recovery; and an azetidinone compound having a low content of impurity, and which has a controlled particle size distribution of crystals and improved handleability and stability. The crystallization is carried out by adding a hydrocarbon solvent to a solution in which an azetidinone compound extremely useful as a common intermediate for the synthesis of 1β-methylcarbapenem compounds is dissolved in the presence of a seed crystal in an amount of 200% by weight or less based on the weight of the azetidinone compound.

6 Claims, No Drawings

CRYSTALLIZATION METHOD FOR INTERMEDIATES OF CARBAPENEM ANTIBIOTICS

TECHNICAL FIELD

The present invention relates to an improved crystallization method for an azetidinone compound extremely useful as a common intermediate for the synthesis of 1β-methylcarbapenem compounds; a highly-pure azetidinone compound having a low content of an impurity; and an azetidinone compound having a controlled particle size distribution of the crystal and improved handleability and stability.

BACKGROUND ART

A 1β-methylcarbapenem compound exhibits an excellent antibacterial action against a wide range of pathogenic bacteria and also has a high stability in a living body; therefore, the compound is one of the most-watched antibacterial agents. As an intermediate useful for synthesizing the above-mentioned 1β-methylcarbapenem compound, an azetidinone compound represented by general formula (1):

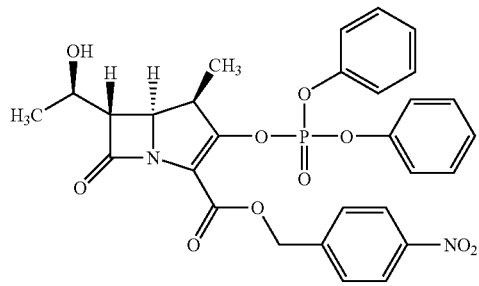

(1)

has been known (see, Patent documents 1, 2 and 3). The compound represented by the formula (1) (hereinafter, sometimes abbreviated as Compound (1)) is a very important and useful intermediate, since the compound generally allows the synthesis of 1β-methylcarbapenem compounds through only two steps of coupling Compound (1) to a thiol compound and deprotecting the resulting intermediate, as described in Patent document 4.

As the method for crystallization of Compound (1), a crystallization method in which n-hexane is added dropwise to a methylene chloride solution containing Compound (1) is disclosed in Patent document 1. Further, a crystallization method in which water is added to a solution of Compound (1) obtained by a synthetic reaction, containing an organic solvent such as ethyl acetate or methylisobutylketone, thereby preparing a mixed solvent and then a poor solvent is added to the mixed solvent is disclosed in Patent document 2. Furthermore, a crystallization method in which a solution of Compound (1) obtained by a synthetic reaction, containing an organic solvent such as ethyl acetate or methylisobutylketone, is washed with water in the presence of methylethylketone, and a water-soluble component is removed by a liquid separation procedure followed by a post-treatment procedure such as condensation, and then, a poor solvent is added to the resulting solution is disclosed in Patent document 3. However, when the present inventors replicated these methods, it was found that the methods have problems such as:

(A) a compound represented by general formula (2):

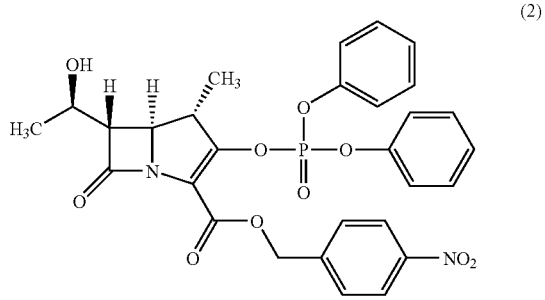

(2)

a compound represented by general formula (3):

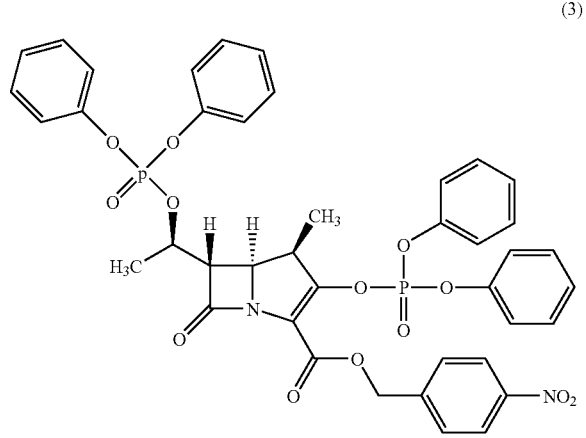

(3)

and/or a compound represented by general formula (4):

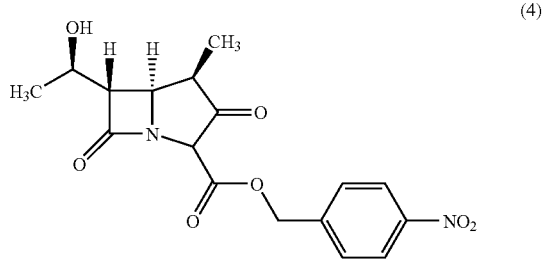

(4)

is contained in the obtained crystal as an impurity in an amount of 0.4% or more; and such a crystal is not sufficiently satisfied in terms of the quality; and it is necessary to control the amount of the impurity to be further reduced, considering the crystal is used as a useful intermediate from which a bulk drug can be synthesized in short steps;

(B) a filtration time is prolonged in the case of industrial scale production because of the poor filterability of the crystal, leading to a decrease in productivity, when the crystallized slurry is subjected to a solid-liquid separation to obtain the crystal; and further, Compound (1) is likely to be decomposed and is unstable in a state of a solution; therefore, the quality is deteriorated due to the increase of the impurity, when the filtration time is prolonged.

Furthermore, it was found that the methods have problems from a practical point of view, such as:

(C) when the present inventors studied the storage stability at 60° C. of Compound (1) in a crystalline form obtained by the same method as described in Patent document 4, 20% decomposition was observed in 8 days, and the stability of Compound (1) under a severe condition such as at 60° C. is low; and therefore, Compound (1) in a crystalline form is not always suitable for a long-term storage in the consideration of industrial scale distribution and storage, although it is disclosed in Patent document 4 that Compound (1) in a crystalline form is not decomposed even if Compound (1) is stored at 40° C. for 20 days and the stability of Compound (1) is extremely high.

Patent document 1: JP 3479720 B
Patent document 2: JP 8-311092 A
Patent document 3: JP 2000-44587 A
Patent document 4: JP 3080417 B

DISCLOSURE OF THE INVENTION

Problems to be Solved by the Invention

As described above, the conventional crystallization methods have problems such as 1) the quality of the crystal is not sufficiently satisfied; 2) the filterability at the time of recovering the crystal is poor, and a filtration time is prolonged in the industrial scale production, leading to a decrease in productivity or quality; 3) the stability of the obtained crystal in a severe condition is low, and the crystal has a problem in long-term storage. Therefore, the conventional methods are not considered to be sufficient as the method for crystallization of Compound (1), and the development of a crystallization method for solving these problems has been demanded.

Means for Solving the Problems

In view of the above circumstances, the present inventors made intensive studies of a crystallization method for solving these problems, and consequently, the present invention was completed. The invention relates to a method for crystallization of a compound represented by the general formula (1), characterized in that a hydrocarbon solvent is added to a solution of the compound represented by the general formula (1) in a presence of a seed crystal in an amount of 200% by weight or less based on a weight of the compound.

Further, the present invention relates to a compound represented by the formula (1), wherein a content of a compound represented by a general formula (2):

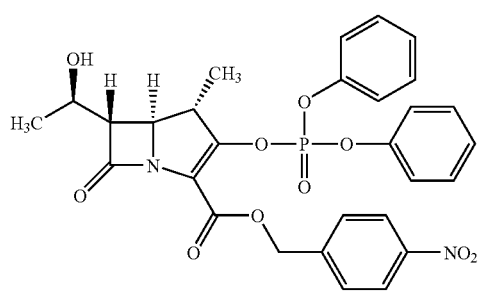

(2)

a compound represented by a general formula (3):

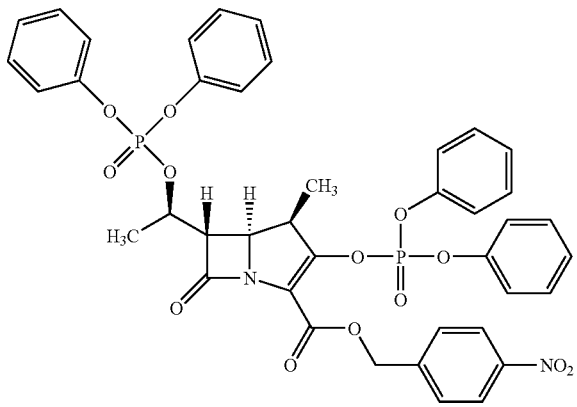

(3)

and/or a compound represented by a general formula (4):

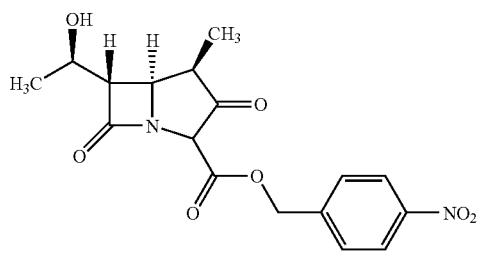

(4)

as an impurity is suppressed to 0.3% or less.

Furthermore, the present invention relates to a compound represented by the formula (1), characterized in that a ratio of a weight of a crystal having a particle size of 350 μm or more is 31% or more in crystals of the compound represented by the formula (1).

In addition, the present invention relates to a compound represented by the formula (1), characterized in that a ratio of a weight of crystal having a particle size of less than 177 μm is 24% or less in a crystal of the compound represented by the formula (1).

Further, the present invention relates to a compound represented by the formula (1), characterized in that a bulk density (a apparent density) of a crystal having a particle size of 500 μm or less is 0.39 or more in a crystal of the compound represented by the formula (1).

Effect of the Invention

According to the method of the present invention, the crystal of the azetidinone compound extremely useful as a common intermediate for the synthesis of 1β-methylcarbapenem compounds, which have a higher quality and a higher stability than conventional crystals and are excellent in filterability at the time of recovering the crystal, can be obtained. Further, the thus obtained compound is an azetidinone compound which has a low content of an impurity and also has a controlled particle size distribution of crystal and improved handleability and stability.

BEST MODE FOR CARRYING OUT THE INVENTION

Hereinafter, the present invention is described in detail.

The present invention is characterized in that a hydrocarbon solvent is added to the solution of the compound represented by general formula (1):

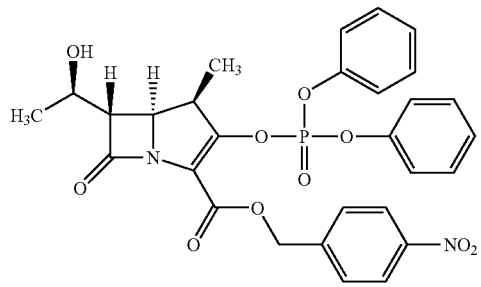

(1)

in a presence of a seed crystal in an amount of 200% by weight or less based on a weight of the compound represented by the formula (1) (hereinafter, sometimes abbreviated as Compound (1)).

First, the solution in which Compound (1) is dissolved is described.

The solution in which Compound (1) is dissolved means a solution in which Compound (1) is dissolved in a rich solvent described below (hereinafter, sometimes abbreviated as a rich solvent solution of Compound (1)). A rich solvent is a solvent having a high solubility for Compound (1), and is described below with specific examples.

A rich solvent is not particularly limited, and examples thereof include, for example, ketones such as acetone, 2-butanone (methylethylketone), 3-methyl-2-butanone, 2-pentanone, 3-pentanone, 4-methyl-2-pentanone (methylisobutylketone) and 2-hexanone; esters such as methyl acetate, ethyl acetate, n-propyl acetate, isopropyl acetate, n-butyl acetate, sec-butyl acetate, isobutyl acetate and tert-butyl acetate; halogenated hydrocarbons such as dichloromethane, chloroform and carbon tetrachloride; alcohols such as n-butanol, n-pentanol and 2-butanol; ethers such as tetrahydrofurane, diethyl ether, dioxane and methyl tert-butyl ether; amides such as N,N-dimethylformamide, N,N-dimethylacetamide, N-methylpyrrolidone and N-ethylpyrrolidone; and nitriles such as acetonitrile. Among the above-mentioned solvents, ketones, esters, halogenated hydrocarbon or a mixed solvent thereof is preferable; and ethyl acetate, isopropyl acetate, dichloromethane, acetone, 2-butanone 4-methyl-2-pentanone or a mixed solvent thereof is more preferable.

A rich solvent solution of Compound (1) to be used in the present invention may be a crude reaction mixture which contains a rich solvent and Compound (1) synthesized by a known method, or a solution prepared by dissolving once isolated Compound (1) in a rich solvent. Further, a rich solvent solution of Compound (1) may be a solution prepared by subjecting a crude reaction mixture of Compound (1) to a post-treatment if necessary, such as washing with water which may contain an acid, a base, a salt or the like; concentration adjustment through condensation; filtration treatment for an insoluble substance; an adsorption treatment with activated carbon as needed. Further, it is needless to say that a solvent other than a rich solvent may be present therein within a range which does not adversely affect the solution. For example, a rich solvent solution of Compound (1) may contain a layer in which an emulsion is formed or may be separated into two layers, as a result of the addition of water for removing a water-soluble component thereto. Furthermore, a hydrocarbon solvent described below may be contained therein.

A concentration of Compound (1) in a rich solvent solution varies depending on a rich solvent to be used and is not particularly limited; however, in general, the concentration is preferably 5 wt % or more, more preferably 8 wt % or more, in consideration of a productivity or recovery rate or the like. Further, in general, the upper limit of the concentration of Compound (1) in a rich solvent solution is preferably not higher than a saturation solubility of Compound (1) in a rich solvent to be used in consideration of a handleability; however, it does not matter that a supersaturated solution is used.

Subsequently, a hydrocarbon solvent to be added to a rich solvent solution in which Compound (1) is dissolved is described.

A hydrocarbon solvent is not particularly limited; however, examples thereof include chain or cyclic aliphatic hydrocarbons having 5 to 20 carbon atoms, aromatic hydrocarbons having 6 to 20 carbon atoms and solvents containing a hydrocarbon, such as Isoper E and Isoper G manufactured by Exxon Chemical Co. Examples of chain or cyclic aliphatic hydrocarbons having 5 to 20 carbon atoms include chain saturated hydrocarbons such as pentane, 2-methylpentane, 2,2-dimethylpentane, n-hexane, isohexane, n-heptane, n-octane, isooctane and n-decane; cyclic saturated hydrocarbons such as cyclopentane, methylcyclopentane, ethylcyclopentane, propylcyclopentane, cyclohexane, methylcyclohexane, ethylcyclohexane and propylcyclohexane; unsaturated hydrocarbons such as 2-pentene, 1-hexene and cyclohexene. Examples of aromatic hydrocarbons having 6 to 20 carbon atoms include benzene, toluene, o-xylene, p-xylene, m-xylene, ethylbenzene and the like. These solvents may be used alone, or two or more types thereof may be used. Among these solvents, a chain or cyclic saturated hydrocarbon is preferred; and n-hexane, n-heptane, cyclohexane or methylcyclohexane is particularly preferred from the viewpoint of being inexpensive and easily obtainable.

Subsequently, a seed crystal and a method for preparing a seed crystal is described.

A seed crystal generally means a small crystal to be used for inducing crystallization from a saturated or supersaturated solution or a supercooled solution. A seed crystal can be added from outside for inducing crystallization; or can be naturally generated; or can be prepared from a supersaturated solution by a concentration gradient, a temperature gradient or a stimulation from outside. Upon crystallization, both of a crystal nucleus generated inside and a crystal nucleus added from outside play a role in promoting a generation of a new crystal nucleus. A process of forming a crystal from a supersaturated solution is divided into two stages: first, a nucleus is generated, and then, the nucleus grows. Crystallization occurs accompanying both phenomena of generation of a crystal nucleus and growth of a crystal nucleus. In general, a deposition of crystal is promoted by adding a seed crystal to a supersaturated solution of a compound to be crystallized. In the present invention, a growth of nucleus is promoted rather than a generation of nucleus by using a seed crystal in an amount greater than that usually used as a seed crystal, thereby a crystal more useful than conventional ones with respect to various aspects such as high purity, stability and handleability can be obtained.

A seed crystal may be separately prepared outside and added to a rich solvent solution of Compound (1), or may be prepared inside in advance. A seed crystal is preferably prepared inside in advance.

In the present invention, the preparation of a seed crystal inside is performed through natural generation, or by a concentration gradient, a temperature gradient, a stimulation from outside or the like. As an inside preparation method, a method in which Compound (1) is deposited by mixing a rich solvent solution of Compound (1) and a hydrocarbon solvent can be exemplified, and a method in which Compound (1) is deposited by adding a hydrocarbon solvent to a rich solvent solution of Compound (1) may be employed, or a method in which Compound (1) is deposited by adding a rich solvent solution of Compound (1) to a hydrocarbon solvent at one time, continuously or in divided portions may be employed. Further, a method in which Compound (1) is deposited by subjecting a rich solvent solution of Compound (1) to a procedure such as condensation, temperature elevation or cooling may be employed. Furthermore, these methods may be combined.

In the case where a seed crystal is prepared inside in advance by mixing with a hydrocarbon solvent, the concentration of Compound (1) is not particularly limited, but may be a concentration at which Compound (1) is supersaturated in a solution containing a rich solvent and a hydrocarbon solvent. By setting a concentration so, deposition of a seed crystal begins generally within 2 hours, preferably within 1 hour, more preferably within 30 minutes.

A temperature when a seed crystal is added and/or prepared is not particularly limited; however, the upper limit thereof is 60° C. or lower, preferably 50° C. or lower, more preferably 40° C. or lower, and the lower limit thereof is −30° C. or higher, preferably −25° C. or higher, more preferably −20° C. or higher, in consideration of the stability of Compound (1) in a rich solvent solution.

A seed crystal is generally added and/or prepared with stirring. An intensity of stirring at the time is not particularly limited, but is generally 0.01 kW/m$^3$ or more, preferably 0.05 kW/m$^3$ or more, more preferably 0.1 kW/m$^3$ or more, further more preferably 0.3 kW/m$^3$ or more, in terms of a required power for stirring per unit volume.

It is preferred from the viewpoint of capable of promoting the growth of crystal nucleus that an aging step is included during and/or after addition of a seed crystal, and/or during and/or after preparation of a seed crystal, when a seed crystal is added and/or prepared. The aging step specifically means a step of performing the above-mentioned stirring procedure or leaving a mixture stand as such without performing a procedure such as addition of separately prepared seed crystal, addition of a hydrocarbon solvent to a rich solvent solution of Compound (1) or addition of a rich solvent of Compound (1) to a hydrocarbon solvent; and means a step of promoting the growth of crystal nucleus. The time of the aging step is not particularly limited, but is suitably 1 minute or more, preferably 10 minutes or more, more preferably 20 minutes or more, further more preferably 30 minutes or more.

An amount of a seed crystal added and/or prepared in a rich solvent solution should be an amount capable of promoting the growth of crystal nucleus when Compound (1) dissolved in a rich solvent solution is crystallized. Upon crystallization, it is general that crystallization is effected by adding an extremely small amount of a seed crystal to a supersaturated solution of a compound to be crystallized; however, in the present invention, crystallization is effected in the presence of a large amount of a seed crystal. In the present invention, the existing amount of a seed crystal in a rich solvent solution of Compound (1) is 200% by weight or less, preferably 150% by weight or less, more preferably 100% by weight or less, based on the weight of Compound (1) dissolved in a rich solvent solution. Further, the lower limit thereof is 1% by weight or more, preferably 5% by weight or more, more preferably 10% by weight or more, as an amount capable of promoting the growth of crystal nucleus when Compound (1) dissolved in a rich solvent solution is crystallized. A weight of Compound (1) dissolved in a rich solvent solution to be used as the basis is an amount of Compound (1) dissolved in a solution after a seed crystal is prepared in the case where a seed crystal is prepared inside. By the above conditions, it becomes possible to improve the filterability and reduce the filtration time by growing crystal nucleus when Compound (1) dissolved in a rich solvent solution is crystallized. Further, the obtained Compound (1) in a crystalline form can be controlled to have a high quality; and moreover, the stability of Compound (1) can also be improved.

Subsequently, the procedure condition when crystallization is effected by adding a hydrocarbon solvent to a rich solvent solution of Compound (1) in the present invention is described.

A liquid amount of a hydrocarbon solvent to be added is not particularly limited, since the solubility of Compound (1) in a mixed solvent of a rich solvent and a hydrocarbon solvent varies depending on the combination with a rich solvent to be used; and it is preferred that the liquid amount is appropriately set such that a crystal of high purity with few impurity can be obtained with maintaining a high recovery rate. In general, the lower limit thereof is preferably 0.01 times or more (v/v), more preferably 0.03 times or more (v/v), particularly preferably 0.05 times or more (v/v), and the upper limit thereof is preferably 10 times or less (v/v), more preferably 5 times or less (v/v), particularly preferably 3 times or less (v/v), based on the amount of a rich solvent solution of Compound (1). In the case where a seed crystal is prepared inside by adding a hydrocarbon solvent, the amount of the hydrocarbon solvent includes also the amount of the hydrocarbon solvent added at the time.

A temperature when a hydrocarbon solvent is added to a rich solvent solution of Compound (1) is not particularly limited; however, the upper limit thereof is 60° C. or lower, more preferably 50° C. or lower, and the lower limit thereof is −30° C. or higher, preferably −25° C. or higher, more preferably −20° C. or higher, in consideration of the stability of Compound (1) in a rich solvent solution.

A method of adding a hydrocarbon solvent is not particularly limited, and a hydrocarbon solvent may be added at one time or sequentially. The sequential addition may be performed by adding a hydrocarbon solvent continuously, or a hydrocarbon solvent is divided into several portions and these portions may be added sequentially. The time taken for the sequential addition varies depending on the temperature, concentration or stirred state upon addition, and is not particularly limited; however, the upper limit thereof is generally within 3 hours, and the addition may be performed within 2 hours, and further may be performed within 1 hour, from the viewpoint of productivity or the like.

The addition of a hydrocarbon solvent is generally performed with stirring. The intensity of stirring at the time is not particularly limited; but is generally 0.01 kW/m$^3$ or more, preferably 0.05 kW/m$^3$ or more, more preferably 0.1 kW/m$^3$ or more, further more preferably 0.3 kW/m$^3$ or more, in terms of a required power for stirring per unit volume.

After a hydrocarbon solvent is added, cooling crystallization or condensation crystallization may be performed in order to increase the recovery rate of a crystal. It is needless to say that a method in which a hydrocarbon solvent is added to a rich solvent solution of Compound (1) and cooling crystallization or condensation crystallization may be appropriately combined and performed. In the case where the boiling point of a rich solvent is lower than that of a hydrocarbon solvent to be added, the recovery rate of a crystal can be increased, by combining with condensation crystallization. Further, even in the case where the boiling point of a rich solvent is higher than that of a hydrocarbon solvent to be added, the solubility of Compound (1) in a mixed solvent of a rich solvent and a hydrocarbon solvent is decreased and the recovery rate of a crystal can be increased, by combining with cooling crystallization.

Compound (1) in a crystalline form obtained by the crystallization method of the present invention can be isolated by a common solid-liquid separation procedure. When a slurry obtained by the crystallization method of the present invention is subjected to a solid-liquid separation procedure, the filterability is much more favorable compared with the case where the slurry obtained by the conventional crystallization method is subjected to a solid-liquid separation procedure. Further, in consideration of industrial scale production of Compound (1), the filtration time can be greatly reduced; therefore, the crystallization method of the present invention is very effective.

Further, in the crystal of Compound (1) obtained by the crystallization method of the present invention, the content of a compound represented by the general formula (2):

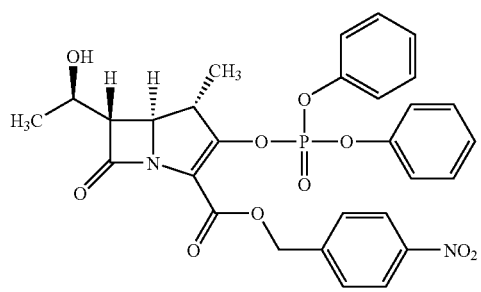

(2)

a compound represented by the general formula (3):

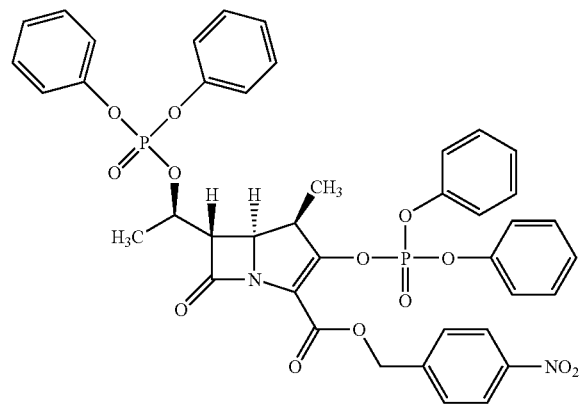

(3)

and/or a compound represented by the general formula (4):

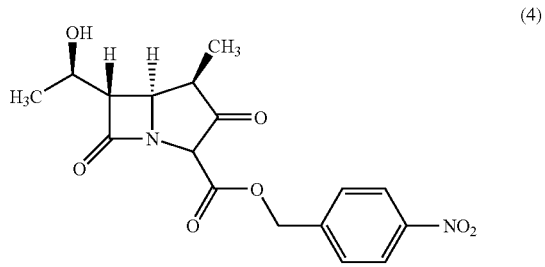

(4)

as an impurity is suppressed to 0.3% or less, and the quality of a crystal is very high. Further, considering the crystal is used as a useful intermediate from which a bulk drug can be synthesized in short steps, the amount of these impurities can be controlled to be smaller; therefore, the crystallization method of the present invention is very useful.

Further, according to the crystallization method of the present invention, the ratio of the weight of a crystal having a large particle size can be increased compared with a crystal of Compound (1) obtained by the conventional method. When particle size distributions were determined for a crystal of Compound (1) obtained by the crystallization method of the present invention and a crystal of Compound (1) obtained by the conventional method, the ratio of the weight of a crystal having a large particle size was higher in the case of the crystal obtained by the crystallization method of the present invention than in the case of the crystal obtained by the conventional method. It is considered that this is because the growth of crystal nucleus can be promoted instead of the generation of new crystal nucleus by effecting crystallization in the presence of a large amount of a seed crystal and particularly performing the aging step in the step of adding a seed crystal and/or preparing a seed crystal inside. According to the crystallization method of the present invention, the ratio of the weight of a crystal having a large particle size can be increased, and it is possible to obtain Compound (1) in which a ratio of the weight of a crystal having a particle size of 350 µm or more is 31% or more. The ratio of the weight of a crystal having a particle size of 350 µm or more is preferably 35% or more, more preferably 40% or more, particularly preferably 45% or more, from the viewpoint of handleability on filtration or the like. Further, according to the crystallization method of the present invention, it is possible to obtain Compound (1) in which a ratio of the weight of a crystal having a particle size of less than 177 µm is 24% or less. The ratio of the weight of a crystal having a particle size of less than 177 µm is preferably 20% or less, more preferably 18% or less, from the viewpoint of handleability on filtration or the like. When the sizes of a crystal of Compound (1) obtained by the crystallization method of the present invention and a crystal of Compound (1) obtained by the conventional method were confirmed with a light microscope, it was found that the crystal obtained by the crystallization method of the present invention is larger than the crystal obtained by the conventional method. As a result of increasing the size of a crystal in this manner and/or controlling the particle size distribution as described above, the filterability at the time of recovering a crystal can be improved; and in the case where the industrial scale production of Compound (1) is performed, problems such as a decrease in productivity and a decrease in quality accompanying an increase in impurity due to prolongation of filtration time can be avoided.

Further, according to the crystallization method of the present invention, a crystal having a particle size larger than that of a crystal obtained by the conventional crystallization method are relatively increased; and as a result, the bulk density is increased. According to the crystallization method of the present invention, for example, it is possible to obtain Compound (1) in which a bulk density of a crystal having a particle size of 500 μm or less is 0.39 or more. The bulk density of a crystal is more preferably 0.40 or more from the following viewpoints. A crystal of the present invention can be handled with a volume smaller than that of a crystal obtained by the conventional crystallization method, leading to reducing the number of containers and transportation cost; therefore, the crystallization method of the present invention is very effective in consideration of distribution in the market.

Furthermore, when the storage stabilities at 60° C. were determined for a crystal of Compound (1) obtained by the crystallization method of the present invention and a crystal of Compound (1) obtained by the conventional method, it was found that the crystal obtained by the crystallization method of the present invention is more stable than the crystal obtained by the conventional method. In the industrial scale production, long-term storage is required in some cases; therefore, a crystal having a higher storage stability is more useful.

As described above, according to the crystallization method of the present invention, it is possible to obtain a useful crystal of Compound (1) which has a higher quality and a higher stability than those of conventional ones, is excellent in filterability at the time of recovering a crystal and has a high bulk density.

EXAMPLES

Hereinafter, the present invention is further clarified with reference to Examples, Comparative examples and Reference examples: however, the invention is not limited thereto.

Reference Example 1

Preparation of a rich solvent solution of p-nitrobenzyl (4R,5R,6S)-1-aza-3-diphenyloxyphosphoryloxy-6-[(1R)-1-hydroxyethyl]-4-methyl-7-oxobicyclo[3.2.0]hept-2-en-2-carboxylate (1)

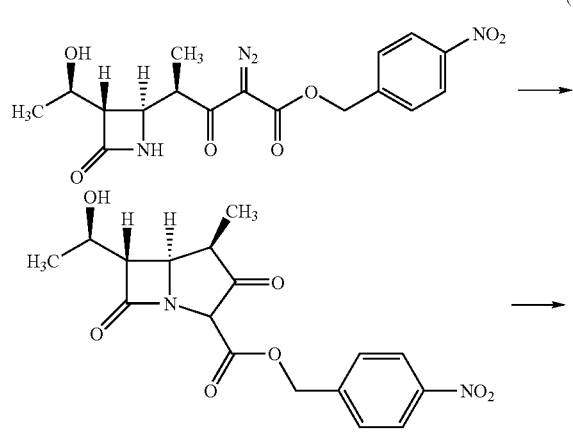

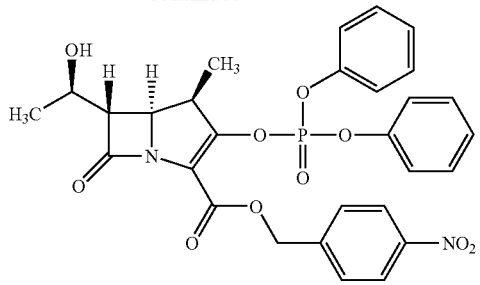

A liquid obtained by dissolving rhodium octanoate (135 mg) in dichloromethane (20 ml) was added to a solution obtained by dissolving (3S,4R)-3-[(R)-1-hydroxyethyl]-4-[(R)-1-methyl-3-diazo-3-(p-nitrobenzyloxycarbonyl)-2-oxopropyl]-2-azetidinone (21.6 g) in dichloromethane (500 ml) under a nitrogen atmosphere, to be reacted at 40° C. for 6 hours. The resulting reaction mixture was cooled to −15° C., and diphenylchlorophosphate (16.4 g) was added thereto at the same temperature. Thereafter, a solution obtained by dissolving N,N-diisopropylethylamine (9.5 g) and N,N-dimethyl-4-aminopyridine (140 mg) in dichloromethane (110 ml) was added dropwise to the reaction mixture at −15° C. over 30 minutes, to be reacted for 30 minutes. The resulting reaction mixture was subjected to washing and liquid separation sequentially with 0.3 N aqueous hydrochloric acid solution (216 ml) and 5% aqueous sodium hydrogencarbonate solution (216 ml) while the temperature was maintained at 10° C. or lower. The obtained organic layer was condensed, thereby 150 ml of a dichloromethane solution containing the titled Compound (1) (30.5 g) was obtained.

Example 1

To the dichloromethane solution which was obtained in Reference example 1 and contained Compound (1) (15.3 g), n-hexane (10 ml) was added at 15° C. over 3 minutes. Crystals were deposited minutes after the addition, and the mixture was aged at the same temperature for 30 minutes. The amount of the deposited crystals after the aging was 25% by weight based on the amount of Compound (1) dissolved in the rich solvent. Subsequently, n-hexane (100 ml) was added dropwise to the rich solvent solution at 15° C. over minutes, and the mixture was aged at the same temperature for 1 hour. After the aging, the resulting slurry was filtered through a filter paper with a diameter of 60 mm and a pore size of 4 μm. The time taken for the filtration was 50 seconds, and the filtration was completed in a shorter time than in the case of Comparative example 1 described below. The obtained crystalline cake was washed sequentially with a mixed solution of dichloromethane (15 ml) and n-hexane (60 ml), and n-hexane (75 ml); and then dried under reduced pressure, thereby the crystal of the titled Compound (1) having a purity of 99% (15.2 g) was obtained. The obtained crystal was arbitrarily taken out and the size of the crystal was observed with a light microscope, it was found that the crystal was larger than the crystal obtained in Comparative example 1.

Comparative Example 1

To the dichloromethane solution which was obtained in Reference example 1 and contained Compound (1) (15.2 g), n-hexane (110 ml) was added dropwise at 15° C. over 30 minutes. The mixture was aged at the same temperature for 1 hour. After the aging, the resulting slurry was filtered through a filter paper with a diameter of 60 mm and a pore size of 4 μm. The time taken for the filtration was 130 seconds. The obtained crystalline cake was washed sequentially with a mixed solution of dichloromethane (15 ml) and n-hexane (60 ml), and n-hexane (75 ml); and then dried under reduced pressure, thereby the crystal of the titled Compound (1) having a purity of 99% (15.1 g) was obtained. The obtained crystal was arbitrarily taken out and the size of crystal was observed with a light microscope.

Reference Example 2

Preparation of a Rich Solvent Solution of p-nitrobenzyl (4R,5R,6S)-1-aza-3-diphenyloxyphosphoryloxy-6-[(1R)-1-hydroxyethyl]-4-methyl-7-oxobicyclo[3.2.0]hept-2-en-2-carboxylate (1)

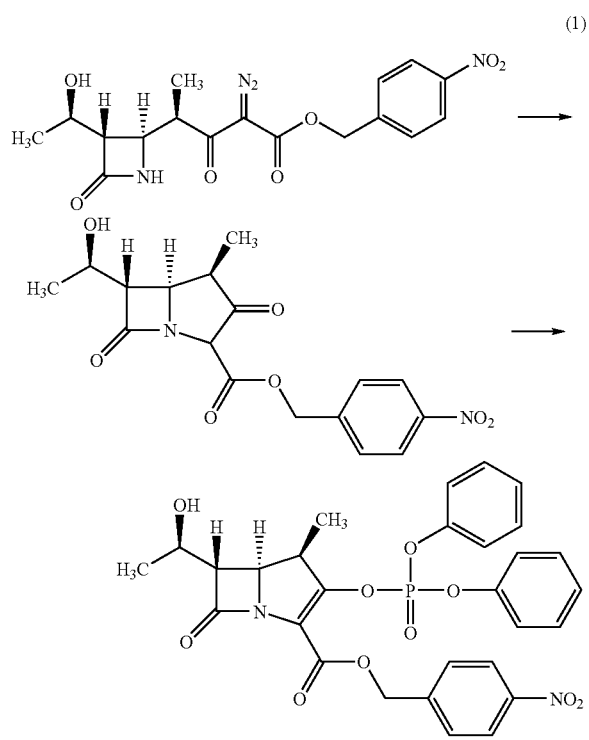

Under a nitrogen atmosphere, (3S,4R)-3-[(R)-1-hydroxyethyl]-4-[(R)-1-methyl-3-diazo-3-(p-nitrobenzyloxy carbonyl)-2-oxopropyl]-2-azetidinone (21.7 g) was added to 4-methyl-2-pentanone (200 ml), and then, methanesulfonic acid (41 mg) and rhodium octanoate (132 mg) were sequentially added thereto, to be reacted 52° C. for 1 hour. The resulting reaction mixture was cooled to −10° C., and diphenylchlorophosphate (16.4 g) and 2-butanone (120 ml) were sequentially added thereto at the same temperature. To the resulting reaction mixture, a solution obtained by dissolving N,N-diisopropylethylamine (9.5 g) and N,N-dimethyl-4-aminopyridine (140 mg) in 2-butanone (120 ml) was added dropwise at −10° C. over 30 minutes, to be reacted for 30 minutes. After the reaction, the resulting reaction mixture was subjected to washing and liquid separation sequentially with 0.3 N aqueous hydrochloric acid solution (200 ml) and 5% aqueous sodium hydrogen carbonate solution (200 ml) at 30° C. or lower, thereby a 4-methyl-2-pentanone/2-butanone mixed solution containing the titled Compound (1) (27.8 g) was obtained.

Example 2

The 4-methyl-2-pentanone/2-butanone solution which was obtained in Reference example 2 and contained Compound (1) (13.9 g) was condensed to 170 ml while the temperature was maintained at 30° C. To the resulting solution, hexane (5 ml) was added at 30° C. over 3 minutes. Crystals were deposited immediately after the addition, and the mixture was aged at the same temperature for 30 minutes. The amount of the deposited crystals after the aging was 194% by weight based on the amount of Compound (1) dissolved in the rich solvent. Subsequently, n-hexane (140 ml) was added dropwise to the rich solvent solution at 30° C. over 40 minutes, and the mixture was aged at the same temperature for 1 hour. After the aging, the resulting slurry was filtered through a filter paper with a diameter of 60 mm and a pore size of 4 μm. The time taken for the filtration was 60 seconds, and the filtration was completed in a shorter time than in the case of Comparative example 2 described below. The obtained crystalline cake was washed sequentially with a mixed solution of 4-methyl-2-pentanone (36 ml) and n-hexane (36 ml), and n-hexane (72 ml); and then dried under reduced pressure, thereby the crystal of the titled Compound (1) having a purity of 99% (12.2 g) was obtained.

Comparative Example 2

The 4-methyl-2-pentanone/2-butanone solution which was obtained in Reference example 2 and contained Compound (1) (13.9 g) was condensed to 170 ml while the temperature was maintained at 30° C. To the resulting solution, n-hexane (145 ml) was added dropwise at 30° C. over 40 minutes, and the mixture was aged at the same temperature for 1 hour. After the aging, the resulting slurry was filtered through a filter paper with a diameter of 60 mm and a pore size of 4 μm. The time taken for the filtration was 190 seconds. The obtained crystalline cake was washed sequentially with a mixed solution of 4-methyl-2-pentanone (36 ml) and n-hexane (36 ml), and n-hexane (72 ml); and then dried under reduced pressure, thereby the crystal of the titled Compound (1) having a purity of 98% (12.4 g) were obtained.

Reference Example 3

Preparation of Rich Solvent Solution of p-nitrobenzyl (4R,5R,6S)-1-aza-3-diphenyloxyphosphoryloxy-6-[(1R)-1-hydroxyethyl]-4-methyl-7-oxobicyclo[3.2.0]hept-2-en-2-carboxylate (1)

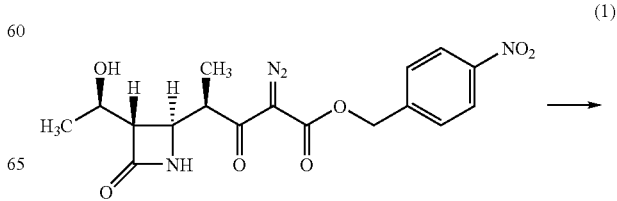

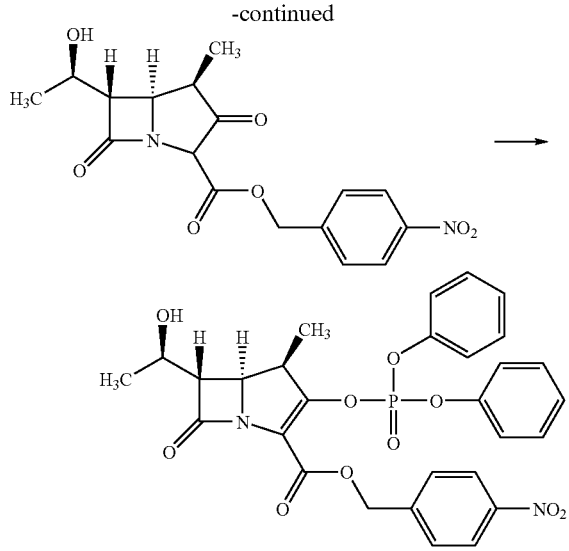

Under a nitrogen atmosphere, (3S,4R)-3-[(R)-1-hydroxyethyl]-4-[(R)-1-methyl-3-diazo-3-(p-nitrobenzyloxy-carbonyl)-2-oxopropyl]-2-azetidinone (25.0 g) was dissolved in ethyl acetate (215 ml), and then, methanesulfonic acid (45 mg) and rhodium octanoate (152 mg) were sequentially added thereto, to be reacted at 52° C. for 2 hours and 30 minutes. The resulting reaction mixture was cooled to −7° C., and diphenylchlorophosphate (18.9 g) and N,N-dimethyl-4-aminopyridine (117 mg) were sequentially added thereto at the same temperature, and then, N,N-diisopropylethylamine (9.3 g) was added thereto over 2 hours. After a reaction was allowed to proceed at −7° C. for 30 minutes, an aqueous solution obtained by dissolving sodium dihydrogenphosphate (5.0 g) and sodium hydrogencarbonate (0.6 g) in water (96 ml) was added to the reaction mixture at 10° C. or lower over 10 minutes. After the addition, the temperature of the mixture was raised to 45° C., thereby a mixed solution of ethyl acetate and water containing the titled Compound (1) (29.8 g) was obtained.

Example 3

The mixed solution of ethyl acetate and water which was obtained in Reference example 3 and contained Compound (1) (14.9 g) was cooled to 20° C., and n-heptane (10 ml) was added thereto at the same temperature over 10 minutes. Crystals were deposited immediately after the addition, and the mixture was aged for 30 minutes. The amount of the deposited crystals after the aging was 150% by weight based on the amount of Compound (1) dissolved in the rich solvent. Subsequently, n-heptane (30 ml) was added dropwise to this rich solvent solution at 20° C. over 30 minutes, and the mixture was cooled to 5° C. and aged for 1 hour. After the aging, the resulting slurry was filtered through a filter paper with a diameter of 60 mm and a pore size of 4 μm. The time taken for the filtration was 5 minutes, and the filtration was completed in a shorter time than in the case of Comparative example 3 described below. The obtained crystalline cake was washed sequentially with a mixed solution of ethyl acetate (11 ml) and n-heptane (9 ml), and water (50 ml); and then dried under reduced pressure, thereby the crystal of the titled Compound (1) having a purity of 98% (13.3 g) were obtained.

Comparative Example 3

The mixed solution of ethyl acetate and water which was obtained in Reference example 3 and contained Compound (1) (14.9 g) was cooled to 20° C., and heptane (40 ml) was added thereto at the same temperature over 30 minutes. Crystals were deposited during the addition, and the mixture was cooled to 5° C. after completion of the addition and then aged for 1 hour. After the aging, the resulting slurry was filtered through a filter paper with a diameter of 60 mm and a pore size of 4 μm. The time taken for the filtration was 8 minutes. The obtained crystalline cake was washed sequentially with a mixed solution of ethyl acetate (11 ml) and n-heptane (9 ml), and water (50 ml); and then dried under reduced pressure, thereby the crystal of the titled Compound (1) having a purity of 98% (13.3 g) were obtained.

Example 4

Measurement of Amount of Impurity

Compound (1) in a crystalline form obtained in each of Example 1, Example 2, Example 3, Comparative example 1, Comparative example 2 and Comparative example 3 was analyzed under the following two analysis conditions. The total amount of impurities of Compound (2), Compound (3) and Compound (4) in the crystals obtained respectively is shown in Table 1. It was found that the amount of the impurities in Compound (1) obtained by the crystallization method of the present invention is smaller than that in Compound (1) obtained by the conventional method.

HPLC Analysis Condition 1:
  Apparatus model: LC-10A series manufactured by Shimadzu Corporation
  Column: ODS column manufactured by GL Science Inc. Inertsil ODS-2 (4.6 mm×150 mm)
  Eluent: acetonitrile/acetic acid buffer (pH 6.0)=1/1 (v/v)
  Flow rate: 1.0 ml/min
  Detection: 254 nm (UV detector)
  Temperature: 25° C.

HPLC Analysis Condition 2:
  Apparatus model: LC-10A series manufactured by Shimadzu Corporation
  Column: Normal phase column manufactured by YMC Co., Ltd.
  YMC-Pack SIL A-003 (4.6 mm×250 mm)
  Eluent: ethyl acetate/n-hexane=2/1 (v/v)
  Flow rate: 0.5 ml/min
  Detection: 270 nm (UV detector)
  Temperature: 25° C.

TABLE 1

|  | Example 1 | Comparative example 1 | Example 2 | Comparative example 2 | Example 3 | Comparative example 3 |
|---|---|---|---|---|---|---|
| Total amount of impurities | 0.26% | 0.44% | 0.28% | 0.60% | 0.30% | 0.64% |

Example 5

Analysis of Stability of the Crystals

About 500 mg of Compound (1) in a crystalline form obtained in each of Example 1 and Comparative example 1 was weighed out in a glass bottle, and the bottle was tightly sealed. Then, the bottle was left in a constant-temperature room at 60° C. for 8 days. The activity on day 1 is set as 100%, and the results obtained by measuring a remaining activity by HPLC are shown in Table 2. It was found that the stability of the crystal obtained in Example 1 is much more favorable than that of the crystal obtained in Comparative example 1.

TABLE 2

|  | Day 1 | Day 4 | Day 6 | Day 8 |
|---|---|---|---|---|
| Crystalline compound of Example 1 | 100% | 97% | 92% | 88% |
| Crystalline compound of Comparative Example 1 | 100% | 96% | 87% | 80% |

Example 6

Measurement of Particle Size Distribution of Crystals

Arbitrarily, 3.0 g of Compound (1) in a crystalline form obtained in each of Example 2, Comparative example 2, Example 3 and Comparative example 3 was taken out. Test sieves with a mesh size in accordance with the Japanese Industrial Standard (JIS Z 8801), having a mesh size of 500 μm, 420 μm, 350 μm, 250 μm, 177 μm, 149 μm, 125 μm, 74 μm or 44 μm and an inner diameter of 8 cm, were used, and were shaken by hand in accordance with the measurement procedure of the standard sieving method specified in JIS Z 8901. The results obtained by comparing the particle size distributions between the "crystal of Example 2" and the "crystal of Comparative example 2", and between the "crystal of Example 3" and the "crystal of Comparative example 3" are shown in Table 3. It was found that the "crystal of Example 2" and the "crystal of Example 3" show a ratio of the weight of crystals remaining on a sieve with a large mesh size higher than the "crystal of Comparative example 2" and the "crystal of Comparative example 3", respectively; and the crystals obtained by the crystallization method of the present invention shows a ratio of crystals having a relatively large particle size higher than the crystals obtained by the conventional methods.

TABLE 3

| Mesh size | Comparative example 2 | Example 2 | Comparative example 3 | Example 3 |
|---|---|---|---|---|
| ≧350 μm | 19% | 49% | 30% | 46% |
| <350, ≧177 μm | 47% | 41% | 45% | 36% |
| <177 μm | 34% | 10% | 25% | 18% |
| Total | 100% | 100% | 100% | 100% |

Example 7

Measurement of Bulk Density of Crystals

Arbitrarily, 3.0 g of Compound (1) in a crystalline form obtained in each of Example 1, Comparative example 1, Example 2 and Comparative example 2 was taken out, and was passed through a test sieve with a diameter of 8 cm and a mesh size of 500 μm in accordance with the Japanese Industrial Standard (JIS Z 8801), and the bulk density of the crystals passing through the sieve was measured. The bulk density was measured by taking a volume of 10 ml of crystals passing through the above-mentioned sieve into a measuring cylinder and tapping was performed until the volume did not change. The bulk density was calculated by using "weight of crystals"/"volume of crystals" as a calculation method. The results are shown in Table 4. When comparison was made between the "crystal of Example 1" and the "crystal of Comparative example 1", and between the "crystal of Example 2" and the "crystal of Comparative example 2", it was found that the "crystal of Example 1" and the "crystal of Example 2" have a larger bulk density than the "crystal of Comparative example 1" and the "crystal of Comparative example 2", respectively; and the crystal obtained by the crystallization method of the present invention has a bulk density higher than the crystals obtained by the conventional methods.

TABLE 4

|  | Example 1 | Comparative example 1 | Example 2 | Comparative example 2 |
|---|---|---|---|---|
| Bulk Density | 0.43 | 0.37 | 0.40 | 0.36 |

The invention claimed is:

1. A method for crystallization of a compound represented by formula (1), which comprises,
   mixing a first solution of the compound represented by formula (1):

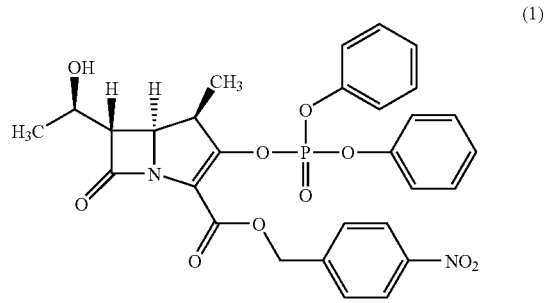

(1)

with a hydrocarbon solvent to form a second solution,
   aging the second solution for 10 minutes or more to form an aged solution containing seed crystals in an amount of 5-200% by weight based on the weight of the compound represented by formula (1) dissolved in the aged solution, and
   adding hydrocarbon solvent to the aged solution in the presence of the seed crystals.

2. The crystallization method according to claim 1, wherein the amount of the seed crystals is 10-200% by weight based on the weight of the compound represented by the formula (1) dissolved in the aged solution.

3. The crystallization method according to claim 1, wherein the hydrocarbon solvent is added continuously or in divided portions to the aged solution.

4. The crystallization method according to claim 1, wherein the first solution is prepared by dissolving the compound of formula (1) in one or more solvents selected from the group consisting of ketones, esters and halogenated hydrocarbons.

5. The crystallization method according to claim 1, wherein the amount of the seed crystals is 5-150% by weight based on the weight of the compound represented by the formula (1) dissolved in the aged solution.

6. The crystallization method according to claim 1, wherein a ratio of a total weight of crystals having a particle size of 350 μor more to a total weight of all crystals of the compound represented by the formula (1) is 31% or more.

* * * * *